United States Patent [19]

Kronberg

[11] Patent Number: 4,993,425
[45] Date of Patent: Feb. 19, 1991

[54] ADAPTER ASSEMBLY FOR USE WITH A CRANIAL BIOSENSOR

[75] Inventor: Harald Kronberg, Staufen, Fed. Rep. of Germany

[73] Assignee: Hellige GmbH, Freiburg, Fed. Rep. of Germany

[21] Appl. No.: 441,211

[22] Filed: Nov. 27, 1989

[30] Foreign Application Priority Data

Jan. 5, 1988 [DE] Fed. Rep. of Germany ..... 88100072

[51] Int. Cl.$^5$ .............................................. A61B 5/00
[52] U.S. Cl. .................................... 128/748; 606/198
[58] Field of Search .................... 606/1, 198; 128/748; 604/93, 175

[56] References Cited

U.S. PATENT DOCUMENTS

| | | | |
|---|---|---|---|
| 3,078,064 | 2/1963 | Turnbull | 248/239 |
| 4,062,354 | 12/1977 | Taylor et al. | 128/748 X |
| 4,186,728 | 2/1980 | Van Lotringen | 128/748 X |
| 4,438,773 | 3/1984 | Letterio | 128/748 |
| 4,494,411 | 1/1985 | Koschke et al. | 73/724 |
| 4,572,212 | 2/1986 | Letterio | 128/748 |
| 4,805,634 | 2/1989 | Ullrich et al. | 128/748 |

FOREIGN PATENT DOCUMENTS

| | | |
|---|---|---|
| 0074037 | 8/1982 | European Pat. Off. . |
| 2526073 | 1/1976 | Fed. Rep. of Germany . |
| 2046687 | 2/1971 | France . |
| 2274261 | 6/1974 | France . |
| 87/01041 | 2/1987 | World Int. Prop. O. . |

OTHER PUBLICATIONS

"A New Miniaturized System for Monitoring the Epidural Pressure in Children and Adults," Neuropädiatric, vol. 8, No. 1, 1977, pp. 21-28.
"Intracranial-Pressure Measurement, Bogiet-Schumacher Method", Hellige.
"Extradural Transducer for Monitoring Intracranial Pressure", ACTA Neurochirugica, Springer-Verlag 1977.

Primary Examiner—Lee S. Cohen
Assistant Examiner—John D. Zele
Attorney, Agent, or Firm—John E. Curley; Kenneth J. Stachel; Richard E. Maebius

[57] ABSTRACT

To enable conventional adapter assemblies used to accurately position a removable biosensor, to be used for measurements in the interior of the skull of small children, the disclosed is a support sleeve which ensures an axial length compensation, taking into account the thinner skull bone thickness, and at the same time ensures accurate alignment of the adapter assembly and the biosensor. The support sleeve also ensures a more even distribution of axial thrust forces when the adapter assembly and the biosensor are positioned. The support sleeve comprises an inwardly extending peripheral flange defining an annular space between the flange and a tubular element slidably inserted in the sleeve. A spring element disposed in the space assures adequate anchorage in the skull bone.

4 Claims, 1 Drawing Sheet

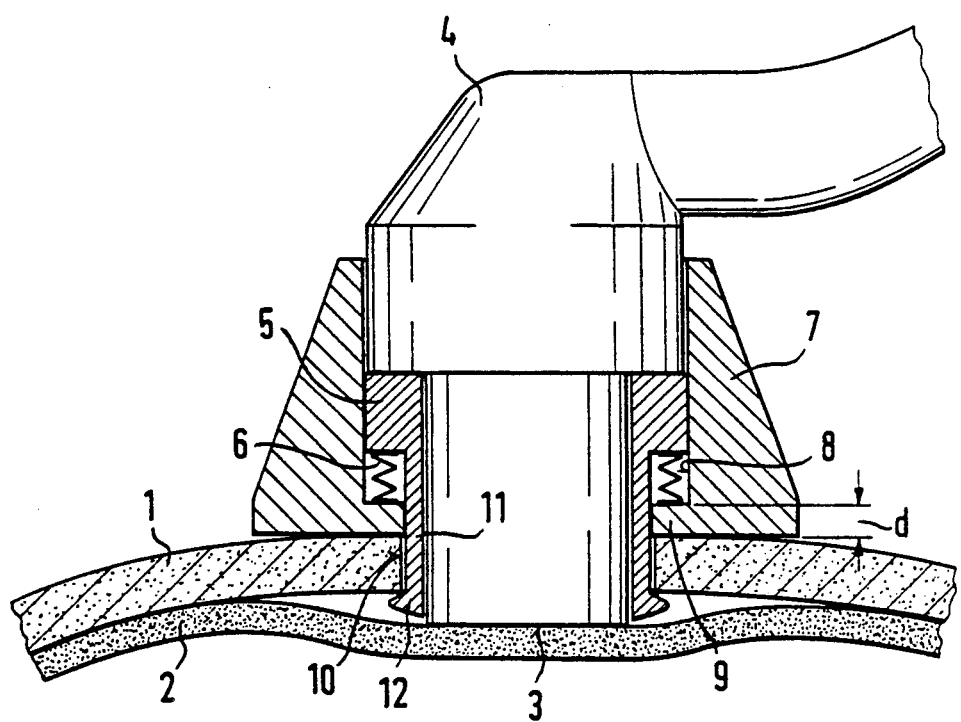

ADAPTER ASSEMBLY FOR USE WITH A CRANIAL BIOSENSOR

This application is a continuation of application Ser. No. 07/292,588 filed Dec. 30, 1988 now abandoned.

FIELD OF THE INVENTION

The invention relates to an adapter assembly for accurately positioning a removable biosensor in the cranium or skull cap.

BACKGROUND OF THE INVENTION

In European Patent Publication No. 0,248,103, an adapter assembly is described, by means of which a biosensor, e.g., a pressure sensor, can be implanted into a hole bored in the skull cap with precisely defined depth spacing and with exactly coplanar alignment of its measurement diaphragm relative to the dura mater (hard meninx, hereinafter called "Dura"). As described in said EP-A1-0,248,103 the surgeon, using a stepped trephine, bores a stepped hole in the skull bone, said hole having a lower narrower diameter proximate the Dura and a upper wider diameter. Into this stepped hole, a spring leg sleeve is then inserted, the downwardly depending lower spring legs being urged outwardly on insertion of the biosensor into the spring leg sleeve (or in a more advantageous embodiment according to EP-A1-0,248,103, by means of a previously inserted expansion sleeve), the retaining cams provided on the lower tips of the spring legs engaging the lower inner periphery of the skull bore hole to ensure axially and radially correct positioning of the biosensor.

Adapter assemblies used to position biosensors for measuring the internal pressure in the skull, transdural or subdural $pO_2$ or $pCO_2$ or for measuring the metabolism in the upper liquor space are as a rule sized to the average thickness of the skull bone of adults, that is to say the axial lengths of the adapter assembly on the one hand and the housing of the biosensor on the other hand are sized to a skull bone thickness of, for example, 3 to 11 millimeters. Increasingly, however, there is also a need for taking measurements using such biosensors, especially pressure sensors, in small children. The thickness of the skull bone in small children is substantially less and the bone is softer than in adults. Thus, the conventional biosensor adapter assemblies can be used for measurements on small children only when very special precautionary measures are observed or not at all.

It is the object of the invention to provide an improved cranial biosensor adapter assembly over that described in EP-A1-0,248,103, whereby a biosensor can be used without problems especially on small children whose bone thickness is less than 3 mm.

DESCRIPTION OF THE INVENTION

In an adapter assembly for the removable implantation of a biosensor into the skull cap of a type described in EP-A1-0,248,103 wherein a tubular spring leg sleeve is inserted into a hole in the skull bone and of which the spring leg ends, facing the interior of the skull, are provided on the outside with retaining cams serving to fix the spring leg sleeve along the inner peripheral edge of the hole, and of which the upper end is stepped outwards and widened to a greater diameter, the invention is characterized by a support sleeve with a bore matching the larger outer diameter of the spring leg sleeve or of the biosensor and with an inward projecting, flange-like peripheral support edge around the front face end of the support sleeve, facing the skull bone, with an axial thickness of the support edge which ensures, in the case of relatively thin skull bones, an axial length compensation between the larger diameter region and the spring leg ends of the spring leg sleeve.

BRIEF DESCRIPTION OF THE DRAWING

The invention and advantageous details are explained in more detail below by reference to the drawing, the single figure of which is a side elevational view, partly in section and shows an illustrative example of a support sleeve according to the invention and its use to accurately align a removable biosensor in the skull cap of small children.

DETAILED DESCRIPTION OF THE INVENTION

In small children, the skull bone 1 is substantially thinner and softer than in adults. Nevertheless, it must be possible to carry out measurements of internal pressures in the skull and also other measurements, of interest in certain clinical procedures, on or through the Dura 2 located underneath. A hole bored by the surgeon in the skull bone is indicated by the reference symbol 10. In order to be able to ensure, especially for measurements of the internal pressure in the skull, that the face of the measuring diaphragm 3 of the pressure sensor 4 is aligned coplanar to the Dura 2 and that the pressure sensor 4 is inserted without a tilt at the measuring point, an applicator device is used which is known from, for example, the said EP-A1-0,248,103 and which comprises a spring leg sleeve 5, the downwardly depending spring legs 11 of which are inserted into the hole 10 in the skull bone 1 and are then urged outwards by the pressure sensor 4 or, in an advantageous manner by an extension sleeve (not shown) of the type described in EP-A1-0,248,103, in such a way that retaining cams 12 on the lower tips of spring legs 11 of the spring leg sleeve 5 engage the lower periphery of the skull bone defined by the inner edge of the hole 10. The spring leg sleeve 5 thus represents a reliable guide for the pressure sensor 4 and ensures accurate axial and radial alignment of the pressure sensor 4, coupled with an alignment of the measuring diaphragm 3 which is precisely coplanar with the Dura 2. An annular spring element 6 which can be made, for example, of silicone rubber effects a certain axial compensation between the larger upper diameter portion, i.e., the radially outwardly extending flange portion, of the spring leg sleeve 5 and the peripheral edge of the hole 10 in the skull bone 1.

In small children, however, the thickness of the skull bone 1 is still so small that, when conventional adapter assemblies and biosensors are used, the spring leg sleeve 5 and hence the biosensor can no longer be inserted in a stable position into the hole 10 and could penetrate too far into the interior of the skull. According to the invention, in order to overcome the problems described, a support sleeve 7 is used, the axial bore 8 of which is sized so as to slidably engage the greater, upper diameter portion of the spring leg sleeve 5 or, if appropriate, the upper diameter portion of the pressure sensor 4. At the lower end facing the skull bone 1, the support sleeve 7 is provided with an inward-projecting, flange-like peripheral support edge 9, the bore diameter of which is matched to the normally desired bore diameter in the skull bone in adaptation to the available adapter assemblies or biosensors. The axial thickness to the peripheral support edge 9 is chosen such that an axial length compensation between the upper, greater diameter portion of the spring leg sleeve 5 is ensured by the spring element 6, taking into account an average desired fixing force, in such a way that, when the spring leg sleeve 5 is inserted through the support sleeve 7, sufficient anchorage of the retaining cams 12 on the peripheral inner edge of the hole 10 is achieved.

As shown, the support sleeve 7 consists of a body of conical or frustoconical shape, for example of titanium (reusable) or of plastic (disposable component). The base of the frustoconical support sleeve 7 rests on the skull bone 1, resulting in a more even distribution of forces when the biosensor or the applicator device is inserted.

Using the support sleeve according to the invention, it is possible to use conventional biosensors and adapter assemblies without problems for measurements in the interior of the skull, especially in the skulls of small children.

I claim:

1. An adapter assembly for accurately positioning a removable biosensor in a circular hole bored through the skull, said adapter assembly comprising a tubular element having a radially outwardly extending peripheral flange and a plurality of downwardly depending spring-like legs, said legs formed as outwardly extending cams whereby when the body of the biosensor is slidably inserted in the tubular element the spring-like legs are urged into contact with the skull bone defined by the hole therein and the outwardly extending cams engage the periphery of the skull bone proximate the Dura, a sleeve element having an axial bore therethrough sized to slidably engage the flange of the tubular element and having an inwardly extending peripheral flange bearing on the lower portion of the tubular element and defining an annular space between said inwardly extending peripheral flange and the outwardly extending peripheral flange of the tubular element, and a spring element disposed in said annular space whereby when the tubular element is inserted into the sleeve element and the biosensor is inserted therein, the cams of the spring-like legs are assured of adequate anchorage to the skull bone.

2. The adapter assembly of claim 1 wherein the sleeve element is of a generally frustoconical shape, the base of which is adapted to rest on the skull.

3. The adapter assembly of claim 1 wherein the sleeve element is made of non-corrosive material.

4. The adapter assembly of claim 3 wherein the sleeve element is made of titanium, stainless steel or plastic.

* * * * *